(12) United States Patent
Konya et al.

(10) Patent No.: US 10,357,193 B2
(45) Date of Patent: Jul. 23, 2019

(54) PUNCTURING SYSTEM AND LANCET CARRIER TAPE

(71) Applicant: Roche Diabetes Care, Inc., Indianapolis, IN (US)

(72) Inventors: Ahmet Konya, Waldsee (DE); Hans-Juergen Kuhr, Mannheim (DE); Frank Deck, Niderkirchen (DE); Hans List, Hesseneck-Kailbach (DE); Michael Keil, Ludwigshafen (DE); Christian Hoerauf, Oftersheim (DE); Thomas Weiss, Mannheim (DE); Marcus Schlothauer, Eisenach (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 15/339,056

(22) Filed: Oct. 31, 2016

(65) Prior Publication Data
US 2017/0042458 A1    Feb. 16, 2017

Related U.S. Application Data

(63) Continuation of application No. 12/615,563, filed on Nov. 10, 2009, now Pat. No. 9,480,420, which is a (Continued)

(30) Foreign Application Priority Data

May 10, 2007    (EP) .................................... 07009367

(51) Int. Cl.
*A61B 17/32*    (2006.01)
*A61B 5/151*    (2006.01)
(Continued)

(52) U.S. Cl.
CPC ........ *A61B 5/15169* (2013.01); *A61B 5/1411* (2013.01); *A61B 5/1518* (2013.01); (Continued)

(58) Field of Classification Search
CPC .............. A61B 5/15171; A61B 5/1411; A61B 5/15153; A61B 5/1518; A61B 5/15169; A61B 5/15146
See application file for complete search history.

(56) References Cited

U.S. PATENT DOCUMENTS 4,725,016 A   2/1988  Marvelli
6,783,537 B1  8/2004  Kuhr et al.
(Continued)

FOREIGN PATENT DOCUMENTS

DE    1919407 A1   10/1970
DE    2803345 B1    6/1979
(Continued)

OTHER PUBLICATIONS

English Translation of corresponding PCT/EP2008/002923 International Preliminary Report on Patentability.

*Primary Examiner* — Anh T Dang
(74) *Attorney, Agent, or Firm* — Dinsmore & Shohl, LLP (57) ABSTRACT

A puncturing system has a carrier tape carrying multiple lancets, a device housing comprising a conveying facility for moving the lancets into a usage position consecutively by moving the carrier tape in a conveying direction, a puncturing drive for accelerating one of the lancets that is positioned in the usage position in a puncturing motion, an opening in the device housing for touching against a body part in which a puncture is to be made by the puncturing motion of one of the lancets, an actuation facility for driving the conveying facility, and an unlockable interlock compris-
(Continued)

ing a stop that blocks further transport of the carrier tape as soon as one of the lancets has reached the usage position.

16 Claims, 4 Drawing Sheets

Related U.S. Application Data continuation of application No. PCT/EP2008/002923, filed on Apr. 14, 2008.

(51) Int. Cl.
*A61B 5/15* (2006.01)
*A61B 17/3209* (2006.01)

(52) U.S. Cl.
CPC .... *A61B 5/150022* (2013.01); *A61B 5/15107* (2013.01); *A61B 5/15146* (2013.01); *A61B 5/15153* (2013.01); *A61B 5/15171* (2013.01); *A61B 5/15178* (2013.01); *A61B 5/150358* (2013.01); *A61B 5/150412* (2013.01); *A61B 5/150503* (2013.01); *A61B 17/32093* (2013.01)

(56) References Cited

U.S. PATENT DOCUMENTS

| | | | |
|---|---|---|---|
| 7,223,276 B2 * | 5/2007 | List | A61B 5/150259 606/181 |
| 7,815,579 B2 | 10/2010 | Roe | |
| 2003/0199906 A1 | 10/2003 | Boecker et al. | |
| 2005/0090850 A1 | 4/2005 | Thoes et al. | |
| 2005/0154410 A1 | 7/2005 | Conway et al. | |
| 2005/0245845 A1 * | 11/2005 | Roe | A61B 5/15173 600/583 |
| 2005/0245954 A1 | 11/2005 | Roe et al. | |
| 2006/0079811 A1 | 4/2006 | Roe et al. | |
| 2006/0195128 A1 | 8/2006 | Alden et al. | |
| 2006/0216817 A1 | 9/2006 | Hoenes et al. | |
| 2006/0240403 A1 | 10/2006 | List et al. | |
| 2006/0247555 A1 | 11/2006 | Harttig | |
| 2007/0173740 A1 * | 7/2007 | Chan | A61B 5/15146 600/583 |
| 2008/0008989 A1 | 1/2008 | Sacherer | |

FOREIGN PATENT DOCUMENTS

| | | |
|---|---|---|
| DE | 102005013685 A1 | 9/2006 |
| DE | 102006061262 B3 | 4/2008 |
| EP | 1504718 A2 | 2/2005 |
| EP | 1402812 B1 | 3/2006 |
| EP | 1299147 B1 | 8/2006 |
| EP | 1714613 A1 | 10/2006 |
| EP | 1360935 B1 | 12/2006 |
| EP | 1873521 A1 | 1/2008 |
| WO | 02/100274 A1 | 12/2002 |
| WO | 2004060174 A2 | 7/2004 |
| WO | 2005032372 A1 | 4/2005 |
| WO | 2005047861 A2 | 5/2005 |
| WO | 2005107596 A2 | 11/2005 |
| WO | 2007062225 A2 | 5/2007 |

* cited by examiner

PUNCTURING SYSTEM AND LANCET CARRIER TAPE

CROSS-REFERENCES TO RELATED APPLICATIONS

This application is a continuation of U.S. Ser. No. 12/615,563, filed Nov. 10, 2009, which is a continuation of PCT Application No. PCT/EP2008/002923, filed Apr. 14, 2008, which claims priority to European Application No. 07009367.9, filed May 10, 2007.

FIELD OF THE INVENTION

The present invention relates to the field of puncturing systems and lancet carrier tapes.

DESCRIPTION OF RELATED ART

Puncturing systems can include, as a lancet supply, a carrier tape that carries a plurality of lancets. By moving the carrier tape in a conveying direction, the lancets can be consecutively situated in a usage position, in which they can be accelerated by a puncturing drive for a puncturing motion in order to generate a puncturing wound for obtaining a sample of body fluid in a body part that is touched against a housing opening of the puncturing system.

Puncturing systems of this type are used, for example, by diabetics who need to check their blood sugar level multiple times daily and, for this purpose, need a sample of body fluid, usually blood or interstitial fluid, that is obtained from a puncturing wound that is generated with a puncturing system.

Unlike puncturing systems having drum cartridges that typically contain only six or eight lancets, a carrier tape can form a lancet reservoir with a significantly larger number of lancets. Puncturing systems having a lancet reservoir in the form of a carrier tape are therefore advantageous in that a user more rarely needs to make the effort involved in exchanging a carrier tape or, if disposable devices are used, obtaining a new device.

To allow a lancet of a carrier tape to be punctured into a body part that is touched against a housing opening, the lancet must be positioned in a usage position with respect to the housing opening.

In the puncturing system known from German Patent No. 2803345, transport of the carrier tape is effected by driving pins or teeth of a gearwheel engaging equidistantly-spaced openings of the carrier tape. Since the lancets are arranged on the carrier tape in predetermined positions with respect to the openings, the tape transport effected by means of the openings automatically causes the lancets to reach the usage position with sufficient precision.

A puncturing system of the type mentioned above is also known from U.S. Patent Application 2005/0245845 A1. In that puncturing system, a tape transport is cased by a reeling facility that is rotated by hand or by means of an electric motor until a new lancet has reached the usage position. However, an automatic system having an electric motor that gets shut off by means of suitable sensors as soon as a fresh lancet has reached the usage position is very elaborate and expensive. Manual tape transport, in which a user must monitor the motion of the carrier tape and terminate further rotation of the reeling facility as soon as a fresh lancet has reached the usage position, is not user-friendly since a lancet may easily be moved beyond the usage position.

The Applicants of the present invention desired to devise a way that allows lancets in a puncturing system of the type mentioned above to be positioned precisely in a usage position with less effort.

BRIEF SUMMARY OF THE INVENTION

It is against the above background that the present invention provides certain unobvious advantages and advancements over the prior art. In particular, the inventors have recognized a need for improvements in puncturing systems and lancet carrier tapes for use with puncturing devices.

In accordance with one embodiment of the present invention, a puncturing system comprises an unlockable interlock that blocks further transport of a carrier tape as soon as a lancet has reached the usage position. The puncturing system can comprise a puncturing device and exchangeable carrier tapes with lancets. However, the puncturing system can just as well be designed as a puncturing device, in which no provision is made for exchange of a carrier tape and which is intended to be disposed of as soon as all lancets of the carrier tape are spent.

In another embodiment of the invention, a carrier tape comprises blockade elements that act in conjunction with an unlockable interlock of a puncturing device in order to position a lancet in a usage position. These blockade elements can, for example, be holes that are engaged by the interlock in order to prevent further transport of the carrier tape. The blockade elements can just as well, for example, be designed in the form of steps that extend transversely to the longitudinal direction of the carrier tape and hit against a positive stop of the puncturing device as soon as a lancet has reached a usage position.

In an aspect of one of the embodiments of a puncturing system according to the invention, a conveying facility, which can be used to make the lancets reach a usage position consecutively by moving the carrier tape, is preferably driven by a slipping clutch. As soon as a lancet has reached its usage position, further transport of the tape is blocked by an interlock. The slipping clutch then slips through.

This is advantageous in that a driving motion, which is generated using an actuation facility for driving the conveying facility, does not need to be adjusted to the conveying path that is required to position a lancet in the usage position, and can therefore just as well be more extensive. Therefore, the drive of the conveying facility of a puncturing system according to the invention can advantageously be simple in structure and can, for example, also be utilized for other functions, such as tensioning a spring of a puncturing drive that is used to accelerate a lancet that is positioned in the usage position for a puncturing motion.

Slipping clutches are also called safety or overload clutches or couplings. These terms shall be synonymous for the scope of the patent description. Clutches of this type disengage as soon as a torque applied to them exceeds a predetermined limit level and they therefore transmit only torques below said limit level.

In order to bring another lancet into the usage position, the interlock can be disengaged, which can be achieved, for example, by again actuating the actuation facility.

Preferably, the conveying facility of a puncturing system according to the invention comprises a reeling facility that reels the tape and thereby moves it in the conveying direction. In a reeling facility of this type, the angle of rotation required for transport of a lancet into the usage position changes since the tape transport effected by one rotation increases with progressive reeling of the carrier tape because the diameter increases. In order to effect the rotating motion of the reeling facility that is required for positioning of a lancet, it is therefore sufficient for the driving motion of the actuation facility to become smaller as more of the lancets of a carrier tape have been used. Having a slipping clutch allows a repeated identical driving motion of the actuating facility to be utilized for this purpose in advantageous fashion, since the slipping clutch slips after further transport is blocked and the conveying facility is no longer influenced by the remaining driving motion of the actuation facility.

A constant driving motion can be effected, for example, by an actuation facility that comprises a rack, which, for actuation, is shifted in its longitudinal direction by a user. In the simplest case, the length of the driving motion corresponds to the distance by which the rack is shifted in longitudinal direction, for example by an end of the rack that projects from the housing being pressed into the housing always by the same distance.

A driving motion of the conveying facility can also be effected, for example, by a spring, in particular a torsion spring. A spring with a spring force for driving a reeling roller into a desired direction of rotation for the purpose of tape transport, can be pre-tensioned, for example during insertion of a tape cartridge into the puncturing device, or can be assembled by the manufacturer in a pre-tensioned state in the case of a single-use device which is intended to be disposed of after all lancets of its carrier tape have been spent. A puncturing system having a moving spring of this type can be provided to be advantageously compact since there is no need to have a slipping clutch or other measures for compensating for a transport path that depends on the reeling status and is effected by a rotation of a reeling roller. In an embodiment of this type, the unlockable interlock of a puncturing system according to the invention always allows a reeling motion to proceed only until a fresh lancet has reached the usage position. The mechanical system of the puncturing drive, for example, can effect short-term disengagement of the interlock. In particular, the returning motion of a lancet puncture can be used to effect disengagement of the interlock. It is preferable in this context to make use of a residual energy of the puncturing drive in order to actuate a switching part, for example a rocker switch or similar device that disengages the interlock.

However, if the carrier tape is relatively long, the use of a pre-tensioned moving spring that relaxes gradually with each transport step that makes a fresh lancet reach the usage position can lead to problems, since the spring force is very high initially and decreases only after use of a few lancets. In this case, both the strength of the carrier tape and the quality of the moving spring are subject to high strains. In order to prevent this, the moving spring of the conveying facility of a puncturing system according to the invention is therefore preferably coupled to a free-wheel module, for example a ratchet mechanism. By this means, the moving spring can be tensioned by the user using an actuation element, for example by means of a gear rack. The use of a free-wheel module allows to prevent a returning motion of the actuation element from being transmitted to the moving spring or the reeling facility after a tensioning motion of the actuation element.

An advantageous embodiment of the invention provides the interlock to have a mechanical stop as interlocking element against which a lancet abuts as soon as it has reached the usage position. This allows for particularly precise positioning of the lancets to be achieved. In particular, also unequal distances between the lancets of a carrier tape can be compensated, since the carrier tape is moved by the conveying facility only until further tape transport is blocked by the hitting against the stop and, consequently, a lancet having reached the usage position. Larger tolerances regarding the distances between the lancets being tolerable in the manufacture of the lancet carrier tape renders fabrication simpler and cheaper.

Preferably, the carrier tape is guided through a gap whose clear width is limited by the interlock hitting against it. For the carrier tape to be transported further, the interlock can be disengaged by transiently enlarging the clear width of the gap such that a tape section with a spent lancet can pass through the gap. Subsequently, the clear width of the gap is reduced again such that a fresh lancet abuts against the stop when it reaches the usage position and further transport of the tape is blocked. Transient opening of the gap can be achieved, for example, by means of a link motion.

Preferably, the gap whose clear width is limited by the stop of the interlock, is provided in a coupling head that is moved in the direction of puncturing during a lancet puncture. In this context, it is preferred for the lancets to be arranged transversely to the longitudinal direction of the carrier tape.

In an embodiment of the invention, a moving spring of the conveying facility is tensioned in the same operating step that introduces the energy into a spring of the puncturing drive. For this purpose, it is particularly advantageous to have a common operating element. Successful tensioning of both springs is preferably fed-back to the user by means of an acoustical or visual signal.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE SEVERAL VIEWS OF THE DRAWING

Further details and advantages of the invention are illustrated by means of exemplary embodiments by making reference to the accompanying drawings. In this context, identical and equivalent components are identified by consistent reference numbers. The features described herein can be made the subject of claims either alone or in combination. In the figures:

Skilled artisans will appreciate that elements in the figures are illustrated for simplicity and clarity and have not necessarily been drawn to scale. For example, the dimensions of some of the elements in the figures may be exaggerated relative to other elements to help improve understanding of the embodiments of the present invention.

DETAILED DESCRIPTION OF THE INVENTION

For the purposes of describing and defining the present invention it is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Figure 1:
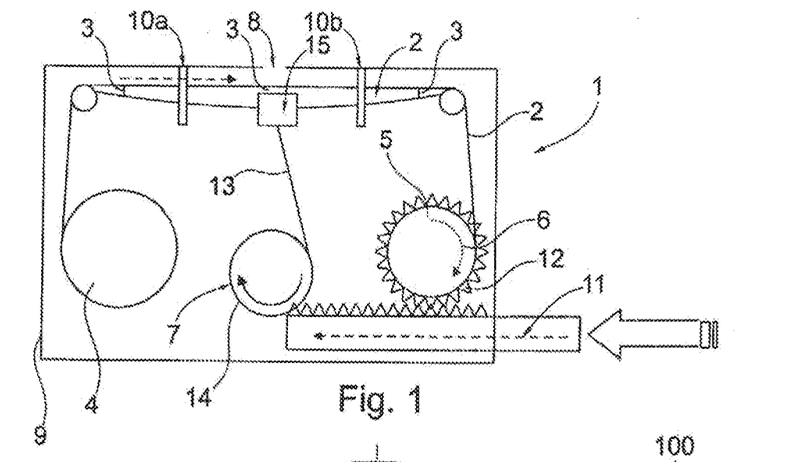
FIG. 1 shows a schematic view of a puncturing system.

FIG. 1 shows a schematic view of a puncturing system 1. The puncturing system 1 includes a carrier tape 2 that carries multiple lancets 3 that are arranged transversely to the longitudinal direction of the tape. A conveying facility 6, which is a reeling facility for driving a roller 5 in the exemplary embodiment shown, can be used to reel and, in the process, move the carrier tape 2 in a conveying direction such that the lancets 3 of the carrier tape 2 reach a usage position consecutively, in which they can be accelerated by a puncturing drive 7 for a puncturing motion in order to puncture into a body part that is touched against a housing opening 8.

In the exemplary embodiment shown, the carrier tape 2 is reeled onto a reservoir roller 4, much like in an audio cassette tape, from which it is unreeled and reeled by-and-by onto the driven reeling roller 5 upon the lancets 3 being spent. The carrier tape 2 can be arranged in a housing 9 to be exchangeable, for example as part of a cartridge, or it can be assembled to be fixed in a device that is disposed of, according to its purpose, as soon as all lancets 3 of the carrier tape 2 have been spent. It is also feasible to use, for example, a stack into which the carrier tape 2 is folded in a zig-zag manner instead of the reservoir roller 4.

During tape transport, the carrier tape 2 with a lancet 3 proceeds past a deflecting facility 10a that twists the carrier tape 2 by 90° before said lancet 3 reaches the usage position. Once a lancet 3 is spent, the corresponding section of the carrier tape 2 is guided past a second deflecting facility 10b that is used to rotate the carrier tape 2 back to its original position.

The conveying facility 6 is driven by an actuation facility 11 that is provided in the form of a gear rack that engages a gearwheel 12 in the exemplary embodiment shown. In order to convey a fresh lancet 3 into the usage position, a user actuates the actuation facility 11; this is effected in the exemplary embodiment shown by pressing the actuation facility 11 in the direction of the arrow shown into the housing 9, i.e. by shifting it along its longitudinal direction.

The actuation facility 11 is coupled to the conveying facility 6 by means of a slipping clutch. In the exemplary embodiment shown, the slipping clutch shown in FIG. 2 acts between the gearwheel 12 and the reeling facility 6. As soon as a lancet 3 has reached the usage position, an unlockable interlock blocks further transport of the carrier tape 2. The slipping clutch is thus made to slip through such that no torque is transferred to the reeling facility 6 any longer.

By this means, upon each actuation, the actuation facility 11 can perform an identical driving motion although the angle of rotation of the reeling facility 6 required for transport of a lancet 3 into the usage position changes, namely decreases, with progressive reeling of the carrier tape 2 onto the reeling roller 5.

The actuation facility 11 is also coupled to the puncturing drive 7. The puncturing drive 7 has an energy storage that supplies the energy required for a puncturing motion and is charged by actuating the actuation facility 11. In the exemplary embodiment shown, the energy storage is a spring, preferably a plastic spring, for example an elastic band, like a rubber band. In the exemplary embodiment shown, the coupling of the actuation facility 11 to the energy storage is effected by means of a wheel 14 that is made to rotate by a motion of the actuating facility 11 and transfers this motion via a connecting rod 13 to a coupling head 15 holding the carrier tape 2.

Figure 2:
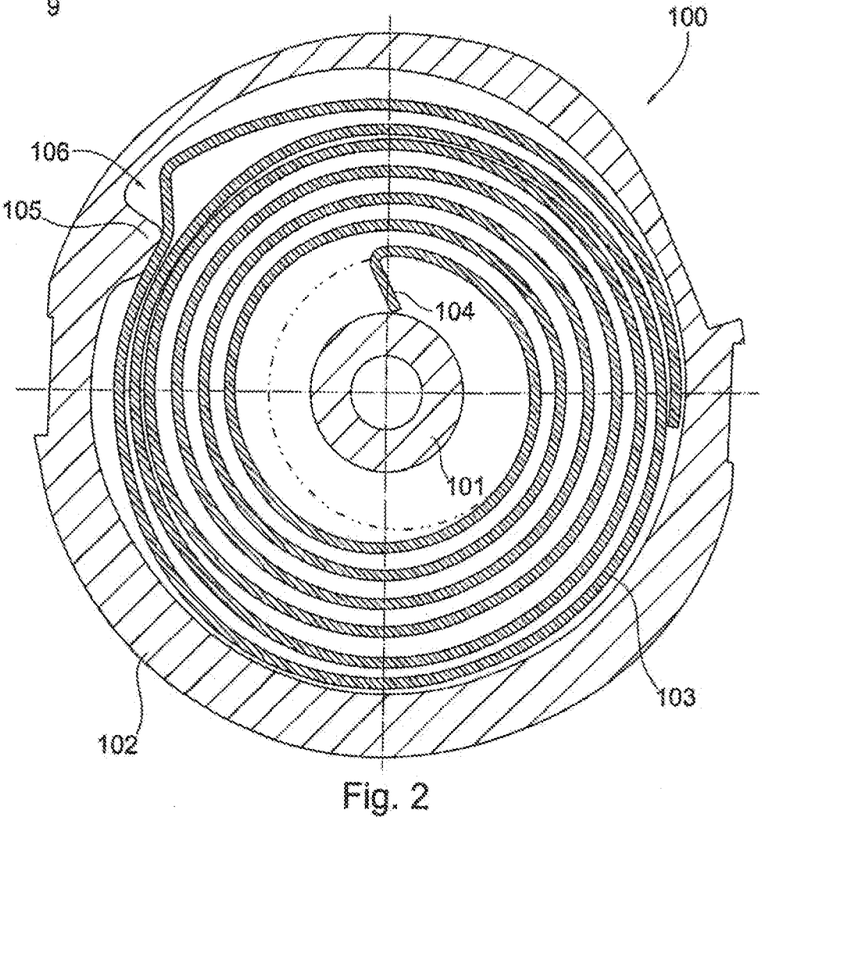
FIG. 2 shows an exemplary embodiment of a slipping clutch.

FIG. 2 shows an exemplary embodiment of a slipping clutch 100. The slipping clutch 100 has an inner shaft 101 that is coupled to the gearwheel 12 shown in FIG. 1, and an outer shaft 102 that envelops the inner shaft 101 in an annular manner and is coupled to the reeling facility 6 of the puncturing system. A helical spring 103 is arranged between the inner shaft 101 and the outer shaft 102. When the inner shaft 101 is rotated, the inner end 104 of the helical spring 103 is taken along and the helical spring 103 is twisted. The inner end 104 can be secured to the inner shaft 101 or touch against it loosely such that a motion of the inner shaft 101 is transferred to the helical spring 103 by frictional forces.

The helical spring 103 touches loosely against the outer shaft 102 such that a torque can be transferred by frictional forces from the helical spring to the outer shaft. Said frictional forces effect a limitation of the maximal transferable torque, since the helical spring 103 slips along the outer shaft 102 when the outer shaft becomes blocked.

In order to increase the maximal transferable torque, the outer shaft 102, as shown in FIG. 2, can have a cam 105 that faces inward and is designed in the form of a projection that faces the helical spring 103. The cam 105 acts in conjunction with a section 106 of the helical spring 103 that is bent such as to be projecting outward such that larger torques can be transferred. If the outer shaft 102 is blocked, the bent section 106 can be deformed and slip past the cam 105.

An interlock that blocks further transport of the carrier tape 2 as soon as a lancet 3 has reached the usage position can be realized in a variety of ways. A first exemplary embodiment of a suitable interlock is illustrated in the following by FIGS. 3 to 6.

Figure 3:
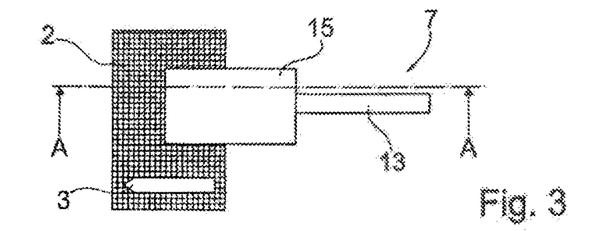
FIG. 3 shows a detailed view of a puncturing drive with a lancet carrier tape prior to reaching a usage position.

FIG. 3 shows a detailed view related to FIG. 1, in which are shown a section of the carrier tape 2 with a lancet 3 prior to reaching the usage position as well as a coupling head 15 of the puncturing drive 7 that is used to transfer a force generated by the puncturing drive 7 to a lancet 3 and the carrier tape 2 connected to it for a puncturing motion. FIG.

Figure 4:
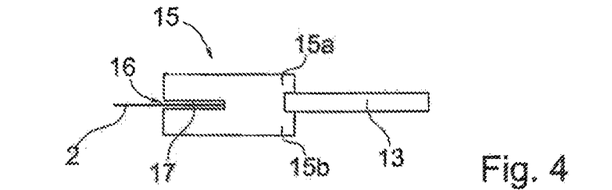
FIG. 4 shows a sectional view related to FIG. 3 taken along the section line A-A.

4 shows a sectional view related to FIG. 3 along the section line A-A. As shown in FIG. 3, the coupling head 15 has a gap 16 through which the carrier tape 2 is guided. The gap 16 is formed by two components 15a, 15b of the coupling head 15 that are mobile with respect to each other. These two components are pressed against each other by spring force. This allows manufacturing tolerances to be favorably compensated.

Figure 5:
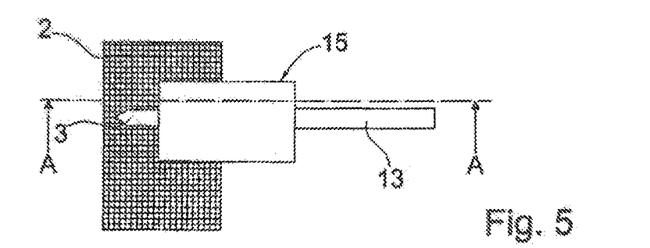
FIG. 5 shows a view according to FIG. 3 with a lancet in the usage position.
Figure 6:
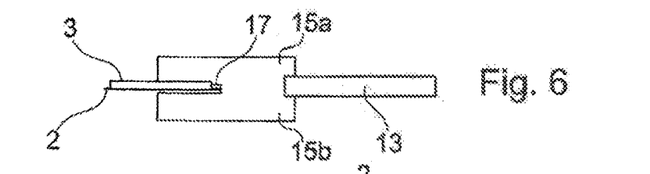
FIG. 6 shows a sectional view related to FIG. 5 taken along the section line A-A.
Figures 7, 8:
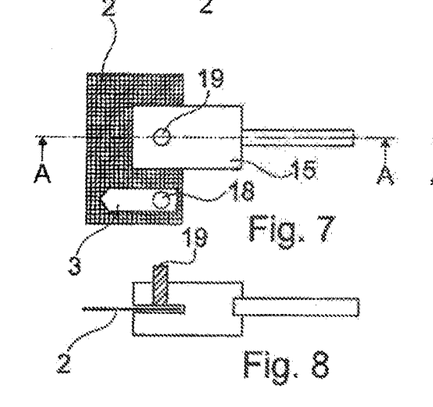
FIG. 7 shows a detailed view of a puncturing drive and a carrier tape prior to reaching the usage position, with an alternative exemplary embodiment of an interlocking mechanism.
FIG. 8 shows a sectional view related to FIG. 7 taken along the section line A-A.
Figures 9, 10:
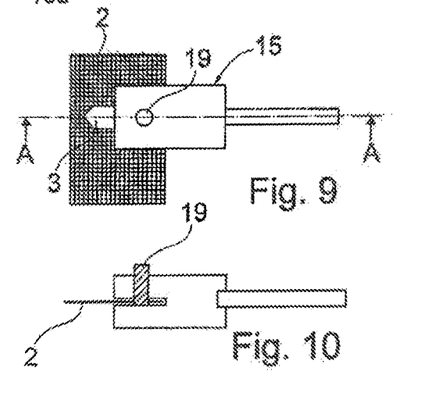
FIG. 9 shows a view according to FIG. 7 with the lancet in the usage position.
FIG. 10 shows a sectional view related to FIG. 9 taken along the section line A-A.

In the position of the two coupling components 15a and 15b that is shown in FIG. 3, the gap 16 has a constriction through which fits the carrier tape 2, but not a lancet 3 that is secured to the carrier tape 2. As soon as a lancet 3 reaches the usage position, said lancet 3 and therefore the carrier tape 2 connected to it is blocked by the constriction of the coupling head 15. This is shown in FIGS. 5 and 6.

The constriction of the gap 16 is formed by a shoulder with a stop surface 17 of the coupling component 15a. In the usage position, the lancet 3 hits against the stop surface 17. The coupling component 15a with the stop surface 17 thus forms an interlocking element that acts in conjunction with a lancet 3 in the usage position. The lancet 3 has a lancet body that forms a step on the carrier tape 2 that extends transversely to the conveying direction. Said step acts in conjunction with the stop surface 17 of the interlock to position a lancet 3 in the usage position.

When a puncture is triggered, the actuation element 11 is returned to its original position, for example by means of a return spring. When the actuation element 11 is actuated again, the interlock is disengaged by the two coupling elements 15a, 15b being moved with respect to each other such that the gap 16 is broadened transiently and the carrier tape 2 can be transported further. One example of how this can be effected shall be illustrated below by means of FIGS. 11 to 14.

FIGS. 7 to 10 show another example of how an interlock can be effected that blocks further transport of the carrier tape 2 as soon as a lancet 3 has reached the usage position. In this example, a hole 18 is provided in the lancet 3 as a blockade element that acts in conjunction with an interlocking element 19 that is designed in the form of a peg and is arranged in the coupling component 15. The stud 19 is movable perpendicularly to the plane of the carrier tape 2. When a lancet 3 reaches the usage position, the stud 19 engages the hole 18 of the lancet 3 such that the lancet 3 and the carrier tape 2 connected to it are blocked.

In order to engage the hole 18 of the lancet 3 reliably, the stud 19 can be pressed against the tape 2, for example, by a spring force. Having a slanted surface on its end engaging the hole 18 allows the stud 19 to be lifted by a lancet 3 reaching the usage position. As soon as the lancet 3 resides in the usage position, the stud 19 then engages the hole 18 of the lancet 3. The hole 18 of the lancet 3 can be designed in the form of a blind hole. However, a through-hole is preferred.

In the interlocking mechanism illustrated by means of FIGS. 7 to 10, the stud 19 forms the interlocking element of the interlock that acts in conjunction with a lancet 3 in the usage position in a form-fitting manner. Thereby the circumferential surface of the stud 19 forms a stop surface against which a lancet 3 in the usage position hits.

Integrating an interlocking element of the interlock into the coupling head 15 that transfers a motion of the puncturing drive to the carrier tape 2, allows for particularly precise positioning of a lancet 3 in the usage position to be achieved, since only the fabrication tolerances of a small number of components affect the accuracy of positioning in this case. The chain of tolerances is advantageously short in the case of an interlocking element in the coupling head 15.

The hole 18 can just as well be arranged in the carrier tape 2 adjacent to a lancet 3. In this case, it is necessary during the manufacture of a carrier tape 2 to ensure that the lancets 3 are always arranged at a predetermined position with respect to a hole 18. This can be attained by generating holes of this type in the carrier tape 2 in a predetermined position with respect to the lancets 3 of the carrier tape 2 only after application of the lancets 3. It is feasible just as well to first generate holes in a carrier tape 2 and to then arrange the lancets 3 in a predetermined position with respect to the holes.

Figure 11:
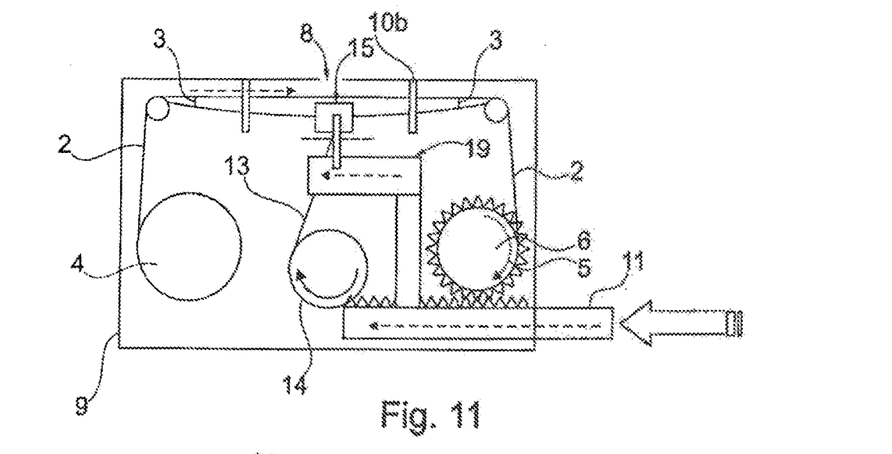
FIG. 11 shows a schematic view of a puncturing system with an actuator for disengaging the interlock.

FIG. 11 shows another schematic view of a puncturing system. FIG. 11 differs from FIG. 1 essentially only by an actuator 19 that is coupled to the actuation facility 11 and serves to transfer the interlock from an interlocking position, in which further transport of the conveyor tape 2 is blocked, to a pass-through position, in which the conveyor tape 2 can be transported further, and back to the interlocking position. Interlocking positions are shown, for example, in FIGS. 6 and 10 for different exemplary embodiments of the interlock.

Figure 12:
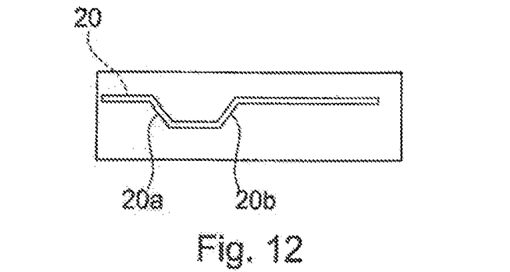
FIG. 12 shows an exemplary embodiment of a motion link for controlling the actuator.

The actuator 19 in the exemplary embodiment shown is coupled to the actuation facility 11 by means of a link motion. An example of the motion link along which the travel proceeds upon actuation of the actuation facility 11 is shown in FIG. 12. The motion link 20 provides a steering curve along which a steering curve slide travels and, in the process, effects brief lifting of the interlocking element that is designed in the form of stud 19 and/or effects a relative motion of the two coupling components 15a, 15b with respect to each other. The actuator 19 and the conveying facility 6 are actuated simultaneously by the actuation facility 11 such that a spent lancet 3 is moved further, away from the usage position, during the brief time the interlock is disengaged. The interlock returns to the interlocking position before a fresh lancet 3 reaches the usage position such that the next lancet 3 is blocked together with the carrier tape 2 connected to it as soon as the next lancet 3 has reached the usage position.

Figure 13:
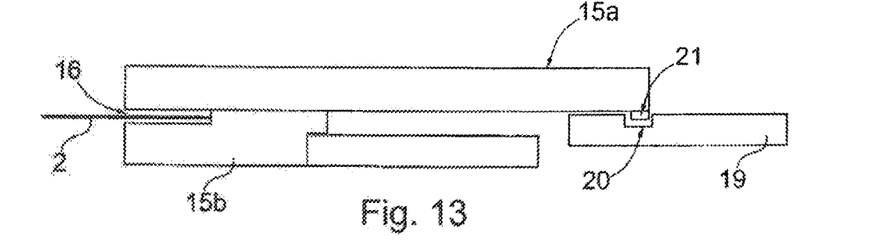
FIG. 13 shows a schematic view of the actuator in the form of a sectional view through the carrier tape.
Figure 14:
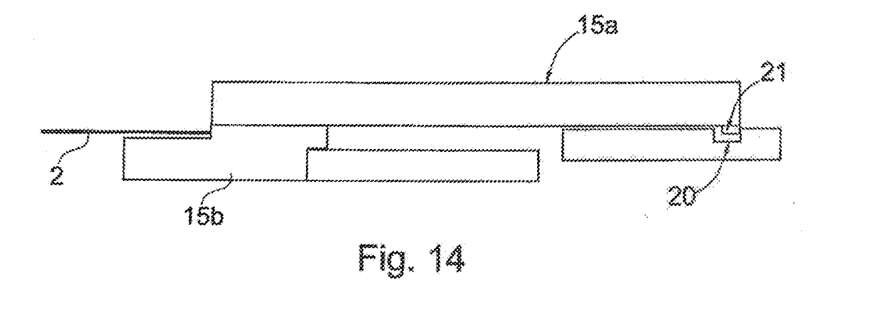
FIG. 14 shows a view according to FIG. 13 with the interlock being disengaged.

FIG. 13 shows a sectional view of the coupling head 15 formed by the two components, 15a, 15b, as well as the actuator 19 with the motion link 20 designed in the form of a groove. A pin 21, as steering curve slide, that is connected to the coupling component 15a engages in the motion link 20. The interlock is shown in the interlocking position in FIG. 13. When the pin 21 travels along the steering curve segment 20a of the motion link 20, the coupling component 15a reproduces the motion predetermined by motion link 20 and is therefore being retracted against the puncturing direction such that it reaches the position shown in FIG. 14, in which the carrier tape 2 and a lancet 3 it carries are no longer clamped in the gap 16. The subsequent steering curve segment 20b returns the interlock to its original position that is shown in FIG. 13.

Aside from coupling the actuator to the actuation facility by means of a bilaterally-guided curve steering, in which a cam follower engages a groove, it is feasible just as well to use a unilaterally-guided cam control to couple the actuator to the actuation facility. In a unilaterally-guided curve steering, the steering curve slide is pressed against a steering curve, which, for example, is a surface with elevations and troughs, over which the steering curve slide glides when it travels along the steering curve. In the simplest case, the steering curve can be a ramp.

Figure 15:
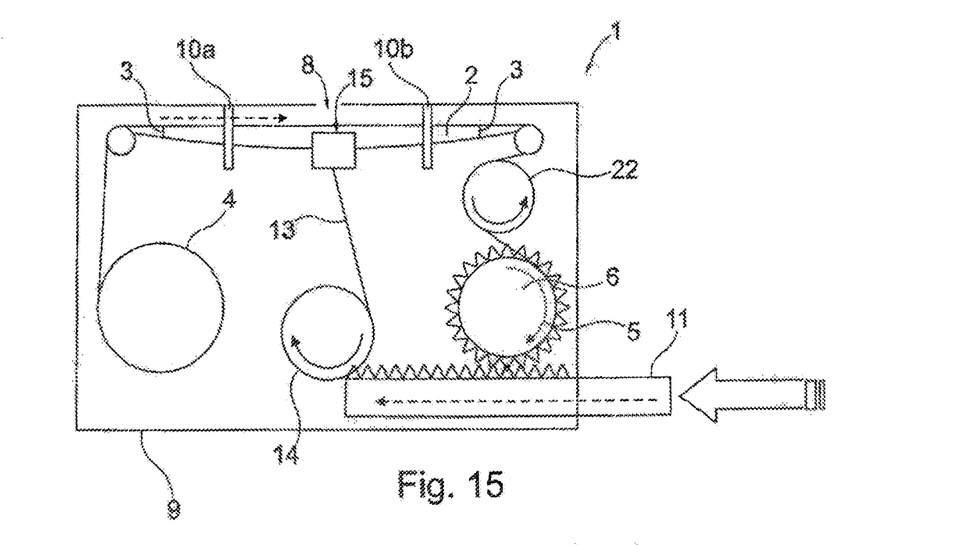
FIG. 15 shows another exemplary embodiment of a puncturing system.

FIG. 15 shows another exemplary embodiment of a puncturing system 1. This exemplary embodiment differs from the exemplary embodiment discussed above in that the carrier tape 2 is coupled to a counting wheel 22, which rotates upon a motion of the carrier tape 2 that is effected by the conveying facility 6, to measure a distance traveled by the carrier tape 2, and becomes blocked as soon as the distance measured has reached the length required to position a lancet 3 in the usage position. Accordingly, the counting wheel 22 forms the interlock in this exemplary embodiment. Preferably, the circumference of the counting wheel 22 is dimensioned such that it corresponds exactly to the distance between two adjacent lancets 3 on the carrier tape 2 and thus the counting wheel 22 becomes blocked in each case after a full rotation. It is feasible just as well for the counting wheel 22 to interlock at any other predetermined position of the angle of rotation or at a predetermined number of rotations. The carrier tape 2 can be prevented from slipping by frictional fit or a perforation of the carrier tape 2 that acts in conjunction with the counting wheel 22.

Figure 16:
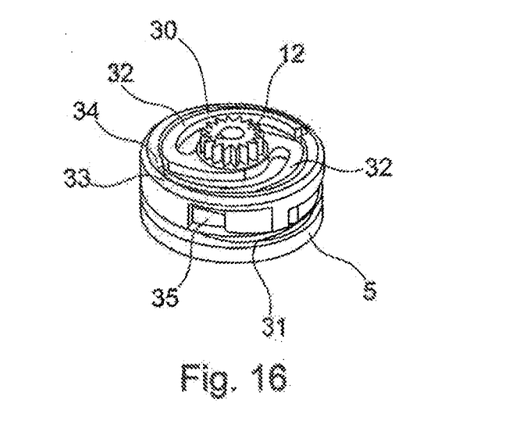
FIG. 16 shows an exemplary embodiment of a free-wheel module.

FIG. 16 shows an exemplary embodiment of a free-wheel module 30 that can be used instead of a slipping clutch 100 in the exemplary embodiment shown in FIG. 1. The free-wheel module 30 has a gearwheel 12 by means of which a rotating motion can be generated, for example by means of a gear rack 11 shown in FIG. 1, in order to tension a torsion spring 31. In the exemplary embodiment shown, upon a motion in a first direction of rotation (clockwise in FIG. 16), the gear rack 12 couples by means of elastic tongues 32 to an enveloping ring 33 by the tongues 32 hitting against steps 34. The ring 33 is coupled to the torsion spring 31 such that rotating the ring 33 in the first direction of rotation tensions the torsion spring 31 that acts on the reeling roller 5.

Once a predetermined angle of rotation is reached, the ring 33 is locked, for example in a form-fitting manner. In the exemplary embodiment shown in FIG. 16, recesses 35 are provided in an external surface of the ring 33 that can be engaged by snap-in elements of a ratchet mechanism in order to lock the ring 33.

The torsion spring 31, which is usually provided in the form of a helical spring, can now relax only by a rotation of the reeling roller 5, but this is possible only when the unlockable interlock illustrated by means of FIG. 1 is disengaged, i.e. when no lancet 3 abuts at the gap 16 of the coupling head 15. As soon as the unlockable interlock is disengaged, the torsion spring 31 relaxes, at least partly, and effects a rotating motion of the reeling roller 5 until a fresh lancet 3 has reached the usage position and the interlock is blocked again.

When the gear rack 11 is returned to its original position after the torsion spring is tensioned, the gearwheel 12 rotates in a second direction of rotation, i.e. counterclockwise in the exemplary embodiment shown. In the process, the tongues 32 glide over the steps 34 of the ring 33 such that the ring 33 does not rotate along. A return spring can be provided in order to move the gear rack 11 back to its original position on its own accord.

As illustrated above, the angle by which the reeling roller 5 must rotate in order to situate a fresh lancet in the usage position depends on how much of the carrier tape has already been reeled onto the reeling roller 5, since this affects the effective diameter of the reeling. The torsion of the torsion spring effected by a tensioning process therefore coincides no more than incidentally with the torsion required for a transport step.

This problem can be addressed, for example, by the gear rack 11 needing to be pressed repeatedly in order to situate a lancet in the usage position, for example two times in the case of a fresh tape with a consequently small diameter of the reeling and only once towards the end of a tape with consequently large diameter of the reeling. However, it is difficult to couple an operating step of this type to the tensioning of the puncturing drive since the respective stroke motions do not coincide and are difficult to synchronize. A solution is offered by an embodiment, in which the spring of the transport drive is pre-tensioned such that said pre-tension is all used up in the middle position (reservoir roller 4 and reeling roller 5 have the same diameter at this point). If the diameter of the reeling roller 5 is small, a larger angle of rotation is required for tape transport and correspondingly more energy for the advancement is taken from the pre-tension. If the diameter of the reeling roller is larger, the situation reverses: each tensioning process now attains an excess of energy that is added up by the torsion spring. In the ideal case, said added-up contribution reaches the level of the initial spring pre-tensioning when the last lancet is reached. Said pre-tensioning can be implemented in the factory, for example in disposable units, or it can be generated by a loading system inserting a tape cartridge. It is advantageous in this context that the angle of rotation can be predetermined during tensioning the torsion spring 31. Consequently, a constant stroke of the gear rack can be realized that is easy to synchronize with the tensioning of the puncturing drive. This facilitates a device that is easy to operate with extremely few operating elements.

Another possibility is to dimension the torsion spring such that it relaxes completely only when a new carrier tape is inserted and the spring force increases incrementally with the individual transport steps, since usually the torsion effected through a tensioning process is used up only in part during a subsequent transport step.

LIST OF REFERENCE NUMBERS

1 Puncturing system
2 Carrier tape
3 Lancet
4 Reservoir roller
5 Reeling roller
6 Conveying facility
7 Puncturing drive
8 Housing opening
9 Housing
10a Deflecting facility
10b Deflecting facility
11 Actuation facility
12 Gearwheel
13 Connecting rod
14 Wheel
15 Coupling head
15a Coupling head component
15b Coupling head component
16 Gap
17 Stop surface
18 Hole
19 Actuator
20 Motion link
20a Steering curve segment
20b Steering curve segment
21 Pin
22 Counting wheel
30 Free-wheel module
31 Torsion spring
32 Tongues 33 Ring
34 Steps
35 Recesses
100 Slipping clutch
101 Inner shaft
102 Outer shaft
103 Helical spring
104 Inner end of helical spring
105 Cam
106 Section of the helical spring that is bent such as to be projecting Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

The invention claimed is:

1. A puncturing system comprising:
a carrier tape that carries multiple lancets,
a device housing comprising a conveying facility for moving the lancets into a usage position consecutively by moving the carrier tape in a conveying direction,
a puncturing drive for accelerating one of the lancets that is positioned in the usage position in a puncturing motion,
an opening in the device housing for touching against a body part in which a puncture is to be made by the puncturing motion of one of the lancets, an actuation facility for driving the conveying facility, and
an unlockable interlock comprising a stop that blocks further transport and movement of the carrier tape relative to the stop in the conveying direction to position one of the lancets ready in the usage position.

2. The puncturing system of claim 1 wherein the interlock can be unlocked by actuating the actuation facility.

3. The puncturing system of claim 1 further comprising a slipping clutch which couples the actuation facility to the conveying facility.

4. The puncturing system of claim 1 wherein the puncturing drive includes an energy storage that supplies the energy required for the puncturing motion and is coupled to the actuation facility such that the energy storage is charged by actuating the actuation facility.

5. The puncturing system of claim 1 wherein the interlock comprises an interlocking element that acts in conjunction with one of the lancets that is in the usage position.

6. The puncturing system of claim 5 wherein the interlocking element acts in conjunction with one of the lancets that is in the usage position in a form-fitting manner.

7. The puncturing system of claim 6 wherein the interlocking element comprises a stop surface against which a lancet abuts in the usage position.

8. The puncturing system of claim 5 wherein the interlocking element comprises a stop surface against which a lancet abuts in the usage position.

9. The puncturing system of claim 1 wherein the interlock can be switched from an interlocking position, in which further transport of the carrier tape is blocked, to a pass-through position, in which the carrier tape can be transported further, by an actuator that is coupled to the actuation facility.

10. The puncturing system of claim 9 wherein the actuator is coupled to the actuation facility by a cam control.

11. The puncturing system of claim 1 wherein the puncturing drive comprises a coupling head that has a gap through which the carrier tape is guided, whereby the unlockable interlock forms a constriction of the gap.

12. The puncturing system of claim 1 wherein the interlock comprises a counting wheel that is coupled to the carrier tape and rotates upon a motion of the carrier tape that is effected by the conveying facility, to measure a distance traveled by the carrier tape, and is blocked as soon as the distance has reached the length required to position a lancet in the usage position.

13. The puncturing system of claim 1 wherein the actuation facility comprises a rack that is shifted in its longitudinal direction by a user in order to actuate the conveying facility.

14. The puncturing system of claim 1 wherein the conveying facility comprises a moving spring.

15. The puncturing system of claim 1 wherein the actuation facility is coupled to the conveying facility by a freewheel module.

16. The puncturing system of claim 1 wherein the lancets each comprises a blockade element that is adapted to act in conjunction with the unlockable interlock to block movement of the carrier tape in the conveying direction.

* * * * *